United States Patent [19]

Bokros

[11] 4,131,957
[45] Jan. 2, 1979

[54] BALL AND SOCKET PROSTHETIC JOINT

[75] Inventor: Jack C. Bokros, Alpine, Calif.

[73] Assignee: General Atomic Company, San Diego, Calif.

[21] Appl. No.: 823,916

[22] Filed: Aug. 12, 1977

[51] Int. Cl.² .................................................. A61F 1/24
[52] U.S. Cl. ........................................ 3/1.91; 3/1.911; 128/92 C
[58] Field of Search ...................... 3/1.9–1.913, 3/1; 128/92 C, 92 CA

[56] References Cited

U.S. PATENT DOCUMENTS

| 3,506,982 | 4/1970 | Steffee | 3/1.91 |
| 3,694,821 | 10/1972 | Moritz | 3/1.911 |
| 3,707,006 | 12/1972 | Bokros et al. | 3/1.9 |
| 3,760,427 | 9/1973 | Schultz | 3/1.91 |
| 3,795,922 | 3/1974 | Herbert et al. | 3/1.911 |
| 3,805,302 | 4/1974 | Mathys | 3/1.91 |
| 3,869,729 | 3/1975 | Attenborough | 3/1.91 |
| 3,952,334 | 4/1976 | Bokros et al. | 3/1.9 X |

Primary Examiner—Ronald L. Frinks
Attorney, Agent, or Firm—Fitch, Even, Tabin & Luedeka

[57] ABSTRACT

A prosthetic joint including a socket-carrying member and a ball-carrying member both of which have stems for insertion into the medullary canals of the bone. The socket has a downwardly extending cylindrical passageway which terminates in a hemispherical bottom surface and a slot which intersects the passageway. The stem of the ball member has generally flat side surfaces and is proportioned to fit through the slot, and the ball has a curvature matching the spherical bottom surface. A shank portion between the ball and stem has a recess where a retainer is snapped onto the shank to lock the members in hinged relationship.

7 Claims, 4 Drawing Figures

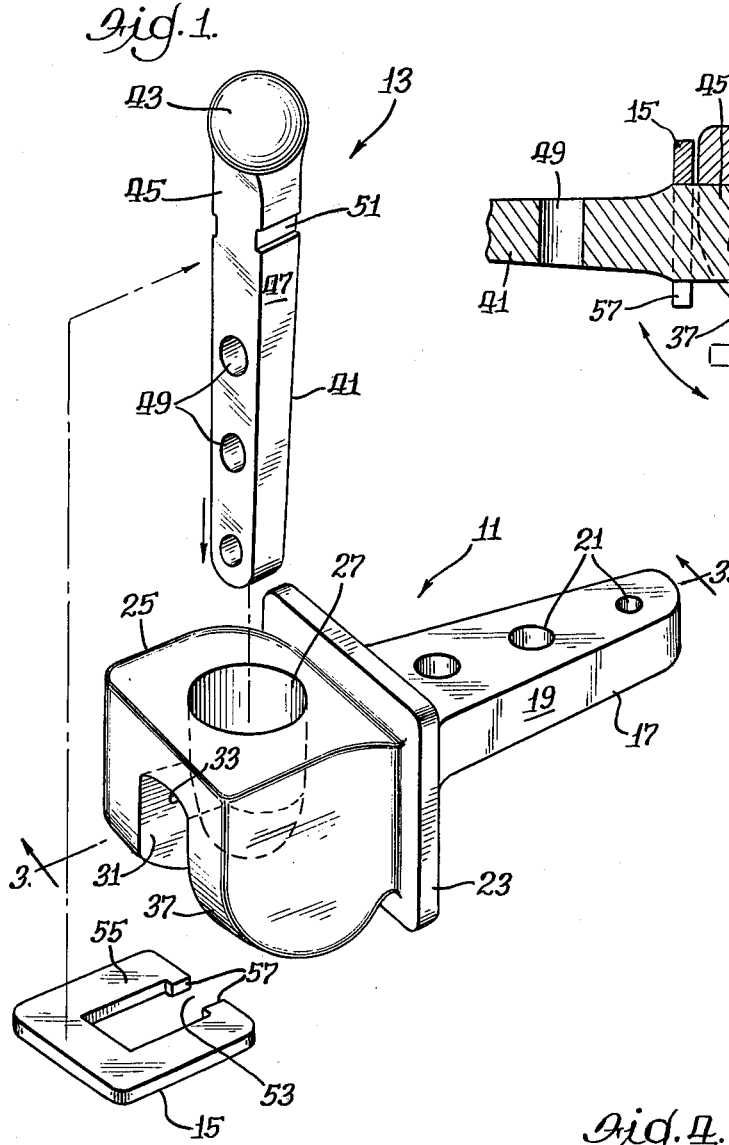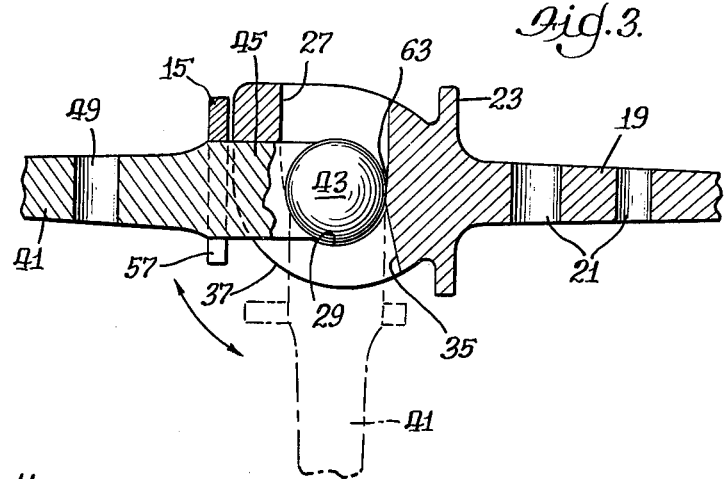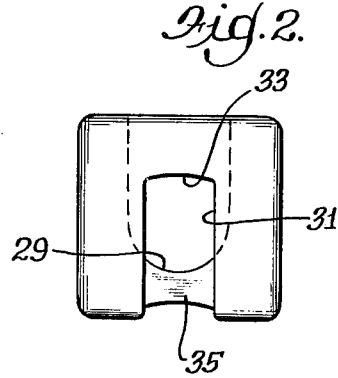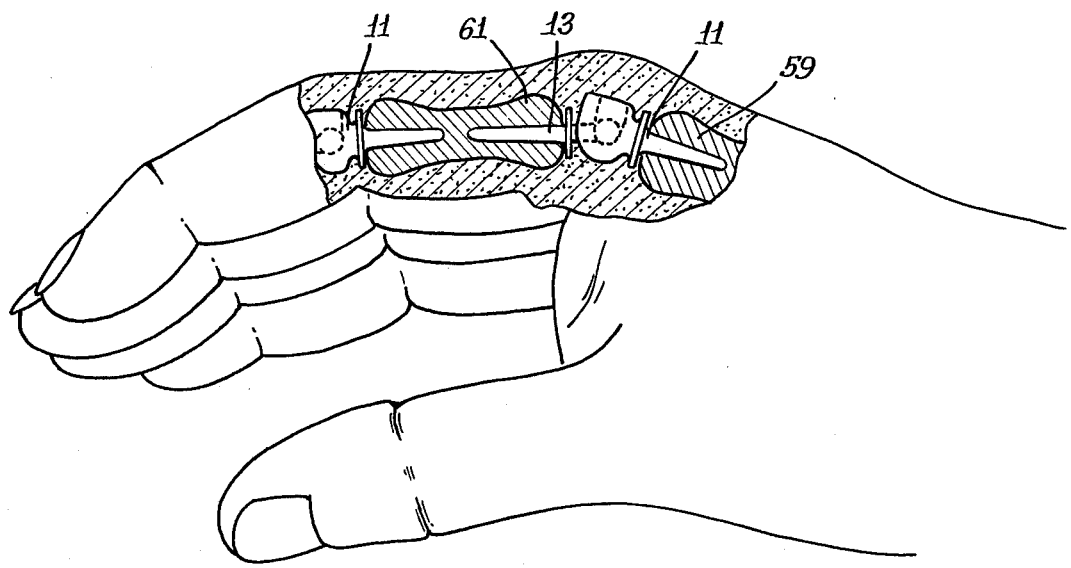

BALL AND SOCKET PROSTHETIC JOINT

This invention relates to prosthetic joints and more particularly to prosthetic joints of the ball-and-socket type.

Various types of prosthetic joints have been developed for the replacement of the metacarpophalangeal joints and the interphalangeal joints of the fingers. Examples of these joints are shown in the following U.S. Pat. Nos.: 3,466,669, issued Sept. 16, 1969; 3,593,342, issued July 20, 1971; 3,760,427, issued Sept. 25, 1973; 3,805,302, issued Apr. 23, 1974; 3,899,796, issued Aug. 19, 1975; 3,990,118, issued Nov. 9, 1976; and 3,991,425, issued Nov. 16, 1976. The same general principles of design apply to the design of elbow joint prostheses, and the following U.S. patents disclose such prostheses: U.S. Pat. Nos. 3,656,186, issued Apr. 18, 1972; 3,879,766, issued Apr. 29, 1975, and 3,990,117, issued Nov. 9, 1976. A knee joint prosthesis utilizes a hinged connection and is related also from the standpoint of the design criteria involved; the following U.S. patents disclose such prostheses: U.S. Pat. Nos. 3,688,316, issued Sept. 5, 1972; 3,707,006, issued Dec. 26, 1972, and 3,765,033, issued Oct. 16, 1973. The design and fabrication of prosthetic joints for fingers, toes, wrists, elbows and knees is a relatively new art, and improvements in such hinged connections are constantly being sought.

The present invention provides an improved prosthetic joint of the ball-and-socket type which, although particularly suited for, and illustrated with respect to, a finger joint, may also be used in the design of joints for toes and the other replacements mentioned above. The design is such that a positive and secure linkage between the two hinged parts is assured, and the flexure stops can be constructed so as to limit flexure or pivoting movement at any angle desired. In addition, motion in more than a single plane can be incorporated within the prosthetic joint.

The invention will be more completely understood from the following detailed description of a preferred embodiment, when read in conjunction with the accompanying drawings wherein:

FIG. 1 is an exploded perspective view of a prosthetic joint embodying various features of the invention;

FIG. 2 is a front view of one portion of the socket-carrying member of the joint shown in FIG. 1;

FIG. 3 is a side section view of the joint, shown in assembled condition, taken generally along the line 3—3 of FIG. 1; and FIG. 4 is a view of a human hand, shown partially in section, which illustrates two prosthetic joints of the type shown in FIG. 1, installed in interphalangeal joints.

As illustrated in exploded perspective in FIG. 1, the invention provides a prosthetic joint which is designed for implantation in a human hand; however, it could be sized for replacement of a joint in a toe. Moreover, the same general design can be incorporated in replacement joints for the elbow, wrist and knee. Basically, the joint includes a socket-carrying member 11, a ball-carrying member 13, and a collar 15. The collar 15 is installed after the two members have been mated and implanted at their desired locations, and it positively locks the two members in operative engagement.

The socket-carrying member 11 includes a stem 17 at one end which is sized and shaped to fit within the medullary canal of the bone after a cavity of suitable proportion has been prepared, using a suitable medical rasp or the like. The stem 17 may be of any suitable shape, but preferably has flat, converging sidewalls 19 so as to assure its remaining at a predetermined relative angular orientation within the bone canal. Several apertures 21 are preferably employed which run from top to bottom and which provide regions into which bone growth can occur so as to firmly secure the prosthetic joint member to the bone in which it is implanted. Preferably, the stem 17 terminates in a flange 23 which abuts the end of the bone adjacent the joint and thus determines the depth to which the stem can be inserted in the medullary canal.

A socket 25 is formed at the other end of the member 11, and it includes a passageway 27 of generally circular cross section which extends downward from the top surface and which terminates in a generally spherical bottom surface 29 that defines a hemispherical cavity, as best seen in FIGS. 2 and 3. The socket 25 contains a slot 31 which intersects with the passageway 27 and which extends from an upper end surface or arcuate stop 33 to a lower end surface or stop 35 which is at an angle past the vertical. Whereas the bottom interior surface 29 is substantially hemispherical, the undersurface 37 of the exterior of the socket, in the direction from front to back, has a curvature of changing radius for a purpose to be described hereinafter.

The ball-carrying element 13 has a stem 41 at one end and a ball 43 at the other. The stem 41 terminates in a shank 45 which is integrally connected to the ball 43. The shank 45 is dimensioned so as to fit within the slot 31 of the socket member, and the stem 41 must also be similarly sized to fit therethrough. The sidewalls 47 of the stem 41 are relatively flat and preferably taper slightly toward the free end to permit its insertion into the scraped-out medullary canal of the bone. The stem 41 also includes three apertures 49 which extend top to bottom and allow for the ingrowth of bone, as described previously. Moreover, the upper and lower surfaces of the stem 41 flare outward at the transition between the end of the stem and the shank 45.

As best seen in FIG. 3, the shank 45 is of substantially constant height, about equal to the ball 43 diameter, and its top and bottom surfaces are curved to match the curvature of the end stops 33,35 as shown in FIG. 2. A pair of grooves 51 are cut in the sidewalls of the shank 45 at its far end where the transition to the stem 41 occurs, and these grooves serve to retain the snap-on collar 15.

The collar 15 may be formed from a flat plate by forming an opening 53 therein which will receive the grooved region of the shank 45. The pair of arms 55 which flank the opening 53 terminate in a pair of bottom detents or lugs 57 which extend toward each other and which form an entry slightly narrower than the width of the shank 45 in the grooved region. The width of the opening 53 is generally made just barely narrower, for example, 0.1 to 0.5 mm., than the thickness of the grooved region of the shank 45 so as to create an interference fit that assures a firmness of joinder between the collar 15 and the ball-carrying member 13. The exact dimensions depend upon the modulus of elasticity of the material used to make the collar.

Before installing the joint, the bone canals are appropriately scraped out to an appropriate depth, height and width to accommodate the stem portions of both members. The socket-carrying member 11 is first inserted into the bone canal. In the illustration shown in FIG. 4, the stem 17 is inserted into the distal end of the metacarpal bone 59. With the member 11 in place with the flange 23 abutting the end of the bone 59, the proximal phalanx 61, into which the member 13 will be inserted, is positioned at about 90° to the metacarpal bone. The stem 41 is inserted downward through the passageway 27, through the slot 31 and into the medullary canal at the proximal end of the proximal phalanx 61 until the ball 43 is firmly seated in the hemispherical cavity at the bottom. To facilitate insertion, the passageway 27 may be enlarged slightly at the upper end and then taper in a frustoconical section 63 just above the hemispherical cavity. The collar 15 is then slid downward in the grooves 51 of the shank 45 until the lugs 57 snap into place below the shank 45.

The installation of the collar 15 positively locks the two members 11,13 together, and the sliding movement of the rear surface of the collar 15 against the curved undersurface 37 of the socket defines the pivoting or flexure movement of the ball-carrying member 13 relative to the member 11. The member 13 will pivot, substantially as a hinge, with respect to the member 11, with the shank 45 being guided by the walls of the slot 31 in which it resides and with the ball 43 being generally seated in the hemispherical cavity at the bottom of the passageway 27. In the straight-out or extended position, the upward movement of the member 13 is limited by the stop 33 at the upper end of the slot, against which the upper surface of the shank will abut. Downward pivoting occurs with flexure of the joint, and the rear surface of the collar 15 slides along the curved undersurface 37 of the socket 25 until the bottom of the shank reaches the stop 35, a total pivoting movement of about 110°. Because of the changing radius of curvature on the undersurface 37 of the socket in planes parallel to the slot, the ball 43 rides upward slightly out of the cavity and away from the hemispherical bottom surface 29 as flexure continues and the stop 55 is approached, thus imitating the normal movement of the finger.

If desired, the width of the slot 31 can be made greater than the thickness of the shank 45 so that the ball and socket joint will allow a limited degree of movement in a direction transverse to the hinged movement which has been heretofore described. Moreover, if desired, either the cavity at the bottom of the socket 25 or the ball 43 or both can be offset from the axial centerline of the stem 17,41 of the respective member 11,13 to achieve the desired relative orientation between the phalanges being interconnected.

The socket-carrying member 11, the ball-carrying member 13 and the snap-on collar 15 are preferably made of biocompatible carbon. Such carbon can be provided by deposition from a vapor atmosphere upon a graphite substrate of suitable size and shape using the method described in U.S. Pat. No. 3,399,969, and biocompatible and nonthrombogenic carbon structures are available from General Atomic's Medical Products Division under the trademark PYROLITE. Alternatively, other suitable substrates such as metals and corrosion-resistant metal alloys, may be coated with biocompatible carbon as described in U.S. Pat. No. 3,952,334. Members made in either manner will have an outer surface of biocompatible carbon and thus are accepted by the surrounding tissue and bone.

The illustrated prosthetic joint is considered to be particularly suitable for fabrication from carbon structures, and important advantages follow from the use of such carbon which offers both chemical inertness to the body tissue and fluids and mechanical compatibility with bone, particularly from the standpoint of its modulus of elasticity. With respect to the collar 15, the lugs 57 can be dimensioned so as to each extend about 0.3 mm. into the opening so that the arms 55 must be spread apart slightly to install the collar on the grooved portion of the shank. PYROLITE carbon has sufficient resiliency to permit such movement without rupture or cracking, and thus it is quite suitable in this respect. Carbon can likewise be coated onto a metal substrate to produce a composite structure that will function satisfactorily.

Although the invention has been described with respect to one preferred embodiment, various changes and modifications as would be obvious to one having the ordinary skill in the art may be made without departing from the scope of the invention which is defined solely by the appended claims. Various of the features of the invention are set forth in the claims which follow.

What is claimed is:

1. A prosthetic joint of the ball-and-socket type which includes a first socket-carrying member and a second ball-carrying member, both of said members having a stem portion at one end thereof for insertion into the medullary canal of the bone and having the socket or the ball formed at the opposite end thereof, said socket including a generally cylindrical passageway which extends downward from an upper surface and which terminates in a bottom surface having a generally spherical shape, said socket containing a slot which intersects said passageway, said slot terminating a substantial distance short of the upper surface of said socket portion, said stem of said second member being proportioned to fit through said slot, said ball portion of said second member being proportioned to be received in said passageway and having a curvature which generally matches the curvature of said generally spherical bottom surface, and retaining means connected to said second member at a shank portion of said second member which interconnects said ball and said stem, which is spaced from said ball a distance at least equal to the distance between the undersurface of said socket and said generally spherical bottom surface, which retaining means locks said first and second members in hinged relationship to each other with said second member stem portion extending out of said slot.

2. A prosthetic joint in accordance with claim 1 wherein said first and second members and said retaining means are formed with exterior surfaces of biocompatible carbon.

3. A prosthetic joint in accordance with claim 1 wherein said shank portion of said second member is provided with a recess for connection with said retaining means.

4. A prosthetic joint in accordance with claim 3 wherein said recess means includes a pair of grooves in opposite side surfaces of said stem portion and wherein said retaining means is a snap-on collar.

5. A prosthetic joint in accordance with claim 4 wherein said snap-on collar includes an opening which is just narrower than the width of said shank in said grooved region to create an interference fit and wherein said collar includes detent means which create an entrance to said opening of a width smaller than said opening whereby said detents lock said collar firmly in place upon said shank.

6. A prosthetic joint in accordance with claim 1 wherein said slot has a width greater than the width of said shank so as to permit limited motion in a direction 90° from the plane of said hinged movement.

7. A prosthetic joint in accordance with claim 1 wherein the undersurface of said socket portion has a changing radius of curvature in planes parallel to said slot which permits movement of said ball upward in said passageway away from said bottom surface during hinged pivoting movement of said members.

* * * * *